(12) United States Patent
Xia (10) Patent No.: US 7,632,677 B2
(45) Date of Patent: Dec. 15, 2009

(54) CELL LINE EXPRESSING MUTATED HUMAN TISSUE-TYPE PLASMINOGEN ACTIVATOR, THE CONSTRUCTING STRATEGY THEREOF AND METHOD OF PREPARING EXPRESSED PROTEIN

(76) Inventor: Jiahui Xia, c/o National Lab of Medical Genetics of China, Central South University, 88 Xiangya Rd., Changsha, Hunan 410078 (CN)

( * ) Notice: Subject to any disclaimer, the term of this patent is extended or adjusted under 35 U.S.C. 154(b) by 297 days.

(21) Appl. No.: 10/363,408

(22) PCT Filed: Feb. 16, 2001

(86) PCT No.: PCT/CN01/00127

§ 371 (c)(1),
(2), (4) Date: Aug. 11, 2003

(87) PCT Pub. No.: WO02/22832

PCT Pub. Date: Mar. 21, 2002

(65) Prior Publication Data

US 2004/0077042 A1  Apr. 22, 2004

(30) Foreign Application Priority Data

Sep. 4, 2000  (WO) .................... PCT/CN00/00260

(51) Int. Cl.
*C12N 5/00* (2006.01)
(52) U.S. Cl. .................. 435/325; 435/252.3; 435/69.1; 435/320.1; 435/6
(58) Field of Classification Search ........................ None
See application file for complete search history.

(56) References Cited

U.S. PATENT DOCUMENTS

| 5,223,422 A | 6/1993 | Weidle et al. |
| 5,501,853 A | 3/1996 | Haigwood et al. |
| 5,656,269 A | 8/1997 | Haigwood et al. |
| 7,247,431 B2 * | 7/2007 | Xia et al. ....................... 435/6 |

FOREIGN PATENT DOCUMENTS

| EP | 199574 A | 10/1986 |
| EP | 0340573 A | 11/1989 |
| EP | 0 838 526 A1 | 4/1998 |
| EP | 1 304 380 A1 | 4/2003 |

OTHER PUBLICATIONS

Wells, Biochemistry, vol. 29, pp. 8509-8517, 1990.*
Heim et al., PNAS, vol. 91, pp. 12501-12504, 1994.*
B.A. Keyt et al., Proc. Natl. Acad. Sci. USA, vol. 91 (Apr. 1994), pp. 3670-3674.

* cited by examiner

*Primary Examiner*—Hope A Robinson
(74) *Attorney, Agent, or Firm*—Birch, Stewart, Kolasch & Birch, LLP (57) ABSTRACT

The invention involves a cell line which can express human mutated tissue-type plasminogen activator (TNK-TPA), and its preparation methods. The collection number of cell lines in this invention is CCTCC C200006. We first used a DNA fragment from the short arms of human group D or group G chromosomes or its homolog to construct a recombinant human source gene vector-TNK-TPA (collection number is CCTC m200032); TNK-TPA gene is then incorporated into the target site in the nucleolus organizing region (NOR) of human group D or G chromosomes in host cell line HT1080; of which the recombinant cell line is attained after screening. The recombinant cell line can be used for manufacturing protein.

2 Claims, 2 Drawing Sheets

SEQUENCE LISTING

<160> NUMBER OF SEQ ID NOS: 3

<210> SEQ ID NO 1
<211> LENGTH: 11162
<212> TYPE: DNA
<213> ORGANISM: Homo sapiens
<220> FEATURE:
<221> NAME/KEY: misc_feature
<222> LOCATION: (1)..(11162)
<223> OTHER INFORMATION: target gene vector

<400> SEQUENCE: 1

```
gggcgaattg ggcccgacgt cgcatgctcc tctagactcg aggaattcta ccgggtaggg      60
gaggcgcttt tcccaaggca gtctggagca tgcgcttaag cagccccgct gggcacttgg     120
cgctacacaa gtggcctctg gcctcgcaca cattccacat ccaccggtag gcgccaaccg     180
gctccgttct ttggtggccc cttcgcgcca ccttctactc ctcccctagt caggaagttc     240
ccccccgccc cgcagctcgc gtcgtgcagg acgtgacaaa tggaagtagc acgtctcact     300
agtctcgtgc agatggacag caccgctgag caatggaagc gggtaggcct ttggggcagc     360
ggccaatagc agctttgctc cttcgctttc tgggctcaga ggctgggaag gggtgggtcc     420
gggggcgggc tcaggggcgg gctcaggggc ggggcgggcg cccgaaggtc ctccggaggc     480
ccggcattct gacgcttcaa aagcgcacgt ctgccgcgct gttctcctct tcctcatctc     540
cggcctttcg acctgcagcg acccgcttaa cagcgtcaac agcgtgccgc agatcttggt     600
```

```
ggcgtgaaac tcccgcacct cttcggcaag cgccttgtag aagcgcgtat ggcttcgtac    660
ccctgccatc aacacgcgtc tgcgttcgac caggctgcgc gttctcgcgg ccatagcaac    720
cgacgtacgg cgttgcgccc tcgccggcag caagaagcca cggaagtccg cctggagcag    780
aaaatgccca cgctactgcg ggtttatata gacggtcctc acgggatggg aaaaccacc     840
accacgcaac tgctggtggc cctgggttcg cgcgacgata tcgtctacgt acccgagccc    900
gatgacttac tggcaggtgc tgggggcttc cgagacaatc gcgaacatct acaccacaca    960
acaccgcctc gaccagggtg agatatcggc cggggacgcg gcggtggtaa tgacaagcgc   1020
ccagataaca atgggcatgc cttatgccgt gaccgacgcc gttctggctc ctcatatcgg   1080
ggggaggct gggagctcac atgccccgcc cccggccctc accctcatct tcgaccgcca    1140
tcccatcgcc gccctcctgt gctacccggc cgcgcgatac cttatgggca gcatgacccc   1200
ccaggccgtg ctggcgttcg tggccctcat cccgccgacc ttgcccggca caaacatcgt   1260
gttgggggcc cttccggagg acagacacat cgaccgcctg gccaaacgcc agcgccccgg   1320
cgagcggctt gacctggcta tgctggccgc gattcgccgc gtttacgggc tgcttgccaa   1380
tacggtgcgg tatctgcagg gcggcgggtc gtggcgggag gattggggac agctttcggg   1440
gacgccgtg cccgccccag ggtgccgagc ccagagcaa cgcgggccca cgaccccata     1500
tcggggacac gttatttacc ctgtttcggg ccccgagtt gctggccccc aacggcgacc    1560
tgtacaacgt gtttgcctgg gccttggacg tcttggccaa acgcctccgt cccatgcacg   1620
tctttatcct ggattacgac caatcgcccg ccggctgccg gacgccctg ctgcaactta    1680
cctccgggat ggtccagacc cacgtcacca ccccggctc cataccgacg atctgcgacc    1740
tggcgcgcac gtttgcccgg gagatggggg aggctaactg aaaacacgaa ggagacaata   1800
ccggaaggaa cccgcgctat gacggcaata aaaagacaga ataaaacgca cgggtgttgg   1860
gtcgtttgtt cataaacgcg gggttcggtc ccagggctgg cactctgtcg ataccccacc   1920
gagacccat tggggccaat acgcccgcgt ttcttccttt tccccacccc acccccaag     1980
ttcgggtgaa ggcccagggc tcgcagccaa cgtcggggcg gcaagccctg ccatagccac   2040
gggccccgtg ggttagggac ggggtccccc atggggaatg gtttatggtt cgtgggggtt   2100
attattttgg gcgttgcgtg gggtcaggtc cacgactgga ctgagcagac agacccatgg   2160
tttttggatg gcctgggcat ggaccgcatg tactggcgcg acacgaacac cgggcgtctg   2220
tggctgccaa acacccccga cccccaaaaa ccaccgcgcg gatttctggc gccgccggac   2280
gaactaaacc tgactacggc atctctgccc cttcttcgct ggtacgagga gcgcttttgt   2340
tttgtattgg tcaccacggc cgagtttccg cgggaccccg gccaggacct gcagaaattg   2400
atgatctatt aaacaataaa gatgtccact aaaatggaag ttttcctgt catactttgt    2460
taagaagggt gagaacagag tacctacatt ttgaatggaa ggattggagc tacggggtg    2520
ggggtgggt gggattagat aaatgcctgc tctttactga aggctcttta ctattgcttt    2580
atgataatgt ttcatagttg gatatcataa tttaaacaag caaaaccaaa ttaagggcca   2640
gctcattcct cccactcatg atctatagat ctatagatct ctcgtgggat cattgttttt   2700
ctcttgattc ccactttgtg gttctaagta ctgtggtttc caaatgtgtc agtttcatag   2760
cctgaagaac gagatcagca gcctctgttc cacatacact tcattctcag tattgttttg   2820
ccaagttcta attccatcag aagctcctta atttttatacc actgacttat tttgaaggct   2880
gctataagaa acagccctat gaaactggta ttttcctact gcaaggtggc tactttaaga   2940
```

```
caattttttca ttgcattcta tcaagggatg tcttattatt atatcattat atcaagtgat    3000
gttataaata gtaagaatca gattaagggc tcatatgtcc ttctttgtat tgactgttga    3060
aaaggtatgg ggccaaattt gtagtttgtc tggaattaca tattttttggg ggtctctatt   3120 atcttcatac ttatcctatc taaattttcc attgccaaat ttccttactt attttttagtt  3180 ttatcctatt gctcatgtat ttttatgtct ccataagtct attttggaaa aaggcagagt    3240
actcataatt ttagtatatc ttttagcttt atgttgccat aaacctttca ttatatacat    3300
gatcaacaac agcaaattat ctcacttcag tatttagttt attattttac aaactgattt    3360
atgattgcta acatgtaact gaaggtatac actattagaa cacagttttc agtagaaagt    3420
agcactgcca ttgagtaaaa aaatgttcta acattagagc aacattctta tacaagtttg    3480
catgttgttt actgaggtct aaagcatgac tacacaaaag gctgaataaa attcagattc    3540
ttacatacac ataaaattgt tttattgaga tgacaaagta tatttattat gccacccaga    3600
atataatcca ctctgataac tgccagtgta tgcacttgct gaagtaactc agtacataaa    3660
tggtagccac aacagttgct gtgcatgaaa gttcttctct tccagattga agagtgtaca    3720
atctaaagca ttttaaaact ttaaatccct tattagctta aatataattt aaaattttag    3780
tttgccgtac ctataatttg tctgtacact aggttactaa gggtgatatg attacatatg    3840
tggatacaaa ataattttaa tggaaaatga aattagggta ctcaacaaag ataaagggta    3900
atgatcatgt acactaaccg tatttgagat tagtttaagc ctggggtagc tatacttatg    3960
tttcacagac cttgagaaga tagggaaaaa aagcttttat caacattgct aaggaacagg    4020
taaaagctaa cattaggtaa ctaagaggtg acataaaaaa gactgaataa aatatcatgg    4080
aggtttcata ataagattgg aaattccata gactaggaga gaaagatcc caaaatatac     4140 atgctcattg ggaaaacagc tagtaagaac aaggagagat ctctatttaa tgatacaata    4200
gtagagttat aatttcctgt atattgtaaa tttcaagcat ttaaacattt tcattgaatt    4260
ataaaatatt atttgtaaaa gaaagaaaaa cagcacaact gcagattaca gatgactaag    4320
atagatgaat catgaaaagg tgctagattg tgagcggata acaatttcac acaggaaaca    4380
gctatgacca tgattacgcc aagctctcga cgggatcgcg gccgcgatcc agacatgata    4440
agatacattg atgagtttgg acaaaccaca actagaatgc agtgaaaaaa atgctttatt    4500
tgtgaaattt gtgatgctat tgcttttattt gtaaccatta taagctgcaa taaacaagtt    4560
ggggtgggcg aagaactcca gcatgagatc cccgcgctgg aggatcatcc agccggcgtc    4620
ccggaaaacg attccgaagc ccaacctttc atagaaggcg gcggtggaat cgaaatctcg    4680
tgatggcagg ttgggcgtcg cttggtcggt catttcgaac cccagagtcc cgctcagaag    4740
aactcgtcaa gaaggcgata gaaggcgatg cgctgcgaat cgggagcggc gataccgtaa    4800
agcacgagga gcggtcagc ccattcgccg ccaagctctt cagcaatatc acgggtagcc     4860
aacactatgt cctgatagcg gtccgccaca cccagccggc cacagtcgat gaatccagaa    4920
aagcggccat tttccaccat gatattcggc aagcaggcat cgccatgggt cacgacgaga    4980
tcctcgccgt cgggcatgct cgccttgagc ctggcgaaca gttcggctgg cgcgagcccc    5040
tgatgctctt cgtccagatc atcctgatcg acaagaccgg cttccatccg agtacgtgct    5100
cgctcgatgc gatgtttcgc ttggtggtcg aatgggcagg tagccggatc aagcgtatgc    5160
agccgccgca ttgcatcagc catgatggat actttctcgg caggagcaag gtgagatgac    5220
aggagatcct gccccggcac ttcgcccaat agcagccagt cccttcccgc ttcagtgaca    5280
acgtcgagca cagctgcgca aggaacgccc gtcgtggcca gccacgatag ccgcgctgcc    5340
```

```
tcgtcttgca gttcattcag ggcaccggac aggtcggtct tgacaaaaag aaccgggcgc    5400
ccctgcgctg acagccggaa cacggcggca tcagagcagc cgattgtctg ttgtgcccag    5460
tcatagccga atagcctctc cacccaagcg gccggagaac ctgcgtgcaa tccatcttgt    5520
tcaaccatgg tggatcgatc caagctccca acacaactat gtcagaagca atgtgagga    5580 gcaactgatc ctacctcacc ttatatgctc tgccctggct cctgccctct ctatcctgtg    5640
tgagcagatt ggcccttacc aaggtgtggc tctacggaat caggcttcgg tgatgacaag    5700
catatttctc cctagaatgc tgtgccactc actggcttag gagtctcagc tctgggtact    5760
ccctctgaat aatgtttgtc cttatctgtg cagagaacac tgtctctaaa gcatcctttt    5820
tggcaacgca tttgctcaat caactactga attggtgtta aaattaattt ccttttttt     5880 ctcattatgc aaataagaaa ttgagaagca agctagcag agatttctat cacacctatc     5940
agggatacac aatttccaag aatttcagaa gtgtttggtg ttcctattaa cataaatccg    6000
gaaataacac ctgagtgaac tgtcttctaa ttcttcaact ggatggcttt ttagtgtaaa    6060
agatgttgaa tactgattga cttttaata attttatagt atatgtcaga aatattgcac     6120
agtccctatt tacatcattc tacagtggtt tttaaaatgt tttaagaata aaaacatga     6180 aaactttatt tgattttct gaggaaataa cttttttggat ttaatttcaa tgaaaccgtt    6240
gataacattt ccctccccaa caatctctgg caacgatccc tcagatttta atgattatgt    6300
attattacct tttaatacaa gtagaataac actcagggaa tttacaacat tgttatttt     6360 cagtaaatac attggttgaa gtttaaaagt ctatccgtag taaacttaca tctttcagga    6420
gcttggtcaa tgtgttctgg acaaagcagg aagatgtgac tgaaatcctg aaaggagccg    6480
gctcctgcag cacaaggata atgatacatc tgggtacatt tctcttcaca gcatttgata    6540
gtggctccaa agtgcttaca aaatgcacat tgctgaaagg ggtaaaggag agaaatctct    6600
ttataaaacc ttgaaaagga atatttaaat ataagctggg aaggtataaa aaactctctg    6660
taacatcaca agtaaacaaa ttgaacctgc aaaatattaa acaaggatt cattaaaaat     6720 aataaaatct acattactca atttagtgct ttgtgtgcta ccaactcatc cttccattca    6780
aattagaaag ttagaatttc attccttata ttttcaaaaa taattgtga agcattttag     6840 aaacaaaacc taaatttttt ttttaaaagc aaatagtaat atggttaaag gggcaggttt    6900
ctatattgag gattattata aagttttaa atcctaccaa aactagtaat aggaacatat     6960
attatttatg agacatatta ctatttttta ccctgcctaa aaataaatac aaataaattc    7020
atcaattata agttaacagg gacacaaatg gttaaagact cacacacaaa aaaaacaaaa    7080
ctacatactt caatgtagca atcaacttca aatttcttaa caaagatgg aaatgttggg     7140 gaaaaaatta gtcatctggt atctttccca tttcaacctg cctccattat cttgcaagtg    7200
gtaaaatgca cagaaataag cctcaaacaa gaggggcagt ctagggcaag tgaacacata    7260
agtcggaaga aattatgtaa aatgttgcat ttacttattc agttttccct tagaatgatt    7320
cacaaactct tcctcattct cccaagtcca ttttgagtat cattttcttt gaagagagtc    7380
tgatgggccc tgtactatac agtatgaaat ctctctgtgg gaaatgacta tctaacataa    7440 attttgttt acaccgttac atggtaccta cttgcttatg ccattacatg atcagtttac    7500
ctttttctca acctaatcca agatccttca attgaggcac tatactatct ttgtatccaa    7560
agcaccaaaa atgctgcttc aaacaggccc taatagatag tgttcctat acatatacca    7620 aaaagactta acttttggtg atcttgtttg tgagtgtggc tcataaacag cttagttgag    7680
```

```
ataactggag cctcatgtag cagagacagt tggaccctgc taacattact gtggatatct    7740
tcacatgtta ctacattgac tttatattct gctaattaac cagggactac agtagttaaa    7800
attataattg ttttcaatgt tttatgtgta aatctgtatc tcacatacta tcaaactctt    7860
cctcactgtc atcagtctac tgcattgaat ccaacataac aaagctaaat gactcctgag    7920
ggctgaatca gaaagaagaa aagaaagaga tacaaaactt tagtcggccc ggtggctcac    7980
acctgtaatc ccagcacttt ggaaggccaa ggcgggcgga tcacgaggtc aggagatcga    8040
gaccatcctg gctgatacag tgaaactcca tctctactga aaatacaaaa aattagctgg    8100
acgtggtggt gggcacctgt agtcccagct actcaggagg ctgaagcagg agaagcttct    8160
aaataactca taaacactaa ttactgttgt gacactttaa ttttatacaa tatttataag    8220
tatacagaat aacatttcag tgctattttg cactcaagg gtattaatgc atagcttgag    8280
tattctatag tgtcacctaa atagcttggc gtaatcatgg tcatagctgt ttcctgtgtg    8340
aaattgttat ccgctcacaa ttccacacaa catacgagcc ggaagcataa agtgtaaagc    8400
ctggggtgcc taatgagtga gctaactcac attaattgcg ttgcgctcac tgcccgcttt    8460
ccagtcggga aacctgtcgt gccagctgca ttaatgaatc ggccaacgcg cggggagagg    8520
cggtttgcgt attgggcgct cttccgcttc ctcgctcact gactcgctgc gctcggtcgt    8580
tcggctgcgg cgagcggtat cagctcactc aaaggcggta atacggttat ccacagaatc    8640
aggggataac gcaggaaaga acatgtgagc aaaaggccag caaaaggcca ggaaccgtaa    8700
aaaggccgcg ttgctggcgt ttttcgatag gctccgcccc cctgacgagc atcacaaaaa    8760
tcgacgctca agtcagaggt ggcgaaaccc gacaggacta taaagatacc aggcgtttcc    8820
ccctggaagc tccctcgtgc gctctcctgt tccgaccctg ccgcttaccg gatacctgtc    8880
cgcctttctc ccttcgggaa gcgtggcgct ttctcatagc tcacgctgta ggtatctcag    8940
ttcggtgtag tcgttcgct ccaagctggg ctgtgtgcac gaaccccccg ttcagcccga    9000
ccgctgcgcc ttatccggta actatcgtct tgagtccaac ccggtaagac acgacttatc    9060
gccactggca gcagccactg gtaacaggat tagcagagcg aggtatgtag gcggtgctac    9120
agagttcttg aagtggtggc ctaactacgg ctacactaga aggacagtat ttggtatctg    9180
cgctctgctg aagccagtta ccttcggaaa aagagttggt agctcttgat ccggcaaaca    9240
aaccaccgct ggtagcggtg gtttttttgt ttgcaagcag cagattacgc gcagaaaaaa    9300
aggatctcaa gaagatcctt tgatcttttc tacggggtct gacgctcagt ggaacgaaaa    9360
ctcacgttaa gggattttgg tcatgagatt atcaaaaagg atcttcacct agatcctttt    9420
aaattaaaaa tgaagtttta atcaatcta aagtatatat gagtaaactt ggtctgacag    9480
ttaccaatgc ttaatcagtg aggcacctat ctcagcgatc tgtctatttc gttcatccat    9540
agttgcctga ctccccgtcg tgtagataac tacgatacgg gagggcttac catctggccc    9600
cagtgctgca atgataccgc gagacccacg ctcaccggct ccagatttat cagcaataaa    9660
ccagccagcc ggaagggccg agcgcagaag tggtcctgca actttatccg cctccatcca    9720
gtctattaat tgttgccggg aagctagagt aagtagttcg ccagttaata gtttgcgcaa    9780
cgttgttggc attgctacag gcatcgtggt gtcacgctcg tcgtttggta tggcttcatt    9840
cagctccggt tcccaacgat caaggcgagt tacatgatcc cccatgttgt gcaaaaaagc    9900
ggttagctcc ttcggtcctc cgatcgttgt cagaagtaag ttggccgcag tgttatcact    9960
catggttatg gcagcactgc ataattctct tactgtcatg ccatccgtaa gatgcttttc    10020
tgtgactggt gagtactcaa ccaagtcatt ctgagaatac cgcgcccggc gaccgagttg    10080
```

-continued

```
ctcttgcccg gcgtcaatac gggataatag tgtatgacat agcagaactt taaaagtgct    10140
catcattgga aaacgttctt cggggcgaaa actctcaagg atcttaccgc tgttgagatc    10200
cagttcgatg taacccactc gtgcacccaa ctgatcttca gcatctttta ctttcaccag    10260
cgtttctggg tgagcaaaaa caggaaggca aaatgccgca aaaagggaa taagggcgac     10320
acggaaatgt tgaatactca tactcttcct ttttcaatat tattgaagca tttatcaggg    10380
ttattgtctc atgagcggat acatatttga atgtatttag aaaaataaac aataggggt     10440
tccgcgcaca tttccccgaa aagtgccacc tgtatgcggt gtgaaatacc gcacagatgc    10500
gtaaggagaa aataccgcat caggcgacgc gccctgtagc ggcgcattaa gcgcggcggg    10560
tgtggtggtt acgcgcagcg tgaccgctac acttgccagc gccctagcgc ccgctccttt    10620
cgctttcttc ccttcctttc tcgccacgtt cgccggcttt ccccgtcaag ctctaaatcg    10680
ggggctccct ttagggttcc gatttagagc tttacggcac ctcgaccgca aaaaacttga    10740
tttgggtgat ggttcacgta gtgggccatc gccctgatag acggtttttc gccctttgac    10800
gttggagtcc acgttcttta atagtggact cttgttccaa actggaacaa cactcaaccc    10860
tatctcggtc tattcttttg atttataagg gattttgccg atttcggcct attggttaaa    10920
aaatgagctg atttaacaaa tatttaacgc gaattttaac aaaatattaa cgtttacaat    10980
ttccattcgc cattcaggct gcgcaactgt tgggaagggc gatcggtgcg ggcctcttcg    11040
ctattacgcc agctggcgaa aggggggatgt gctgcaaggc gattaagttg ggtaacgcca    11100
gggttttccc agtcacgacg ttgtaaaacg acggccagtg aattgtaata cgactcacta    11160
ta                                                                   11162
```

<210> SEQ ID NO 2
<211> LENGTH: 30
<212> TYPE: DNA
<213> ORGANISM: Artificial Sequence
<220> FEATURE:
<223> OTHER INFORMATION: TPCF primer directed to Homo sapiens TNK-TPA gene.

<400> SEQUENCE: 2
atgcatccta ggggaggtcg ctgagtagtg          30

<210> SEQ ID NO 3
<211> LENGTH: 29
<212> TYPE: DNA
<213> ORGANISM: Artificial Sequence
<220> FEATURE:
<223> OTHER INFORMATION: TPCR primer directed to Homo sapiens TNK-TPA gene.

<400> SEQUENCE: 3
tgcatgccta ggtaccccct agagcccag          29

CELL LINE EXPRESSING MUTATED HUMAN TISSUE-TYPE PLASMINOGEN ACTIVATOR, THE CONSTRUCTING STRATEGY THEREOF AND METHOD OF PREPARING EXPRESSED PROTEIN

This application is the national phase under 35 U.S.C. § 371 of PCT International Application No. PCT/CN01/00127 which has an International filing date of Feb. 16, 2001, which designated the United States of America.

SUMMARY OF THE INVENTION

The invention relates to a cell line specifically expressing mutated human tissue-type plasminogen activator (TNK-TPA), the construction strategy for said cell line and application of the cell line in manufacturing recombinant human tissue-type plasminogen activator

BACKGROUND OF THE INVENTION

Human tissue-type plasminogen activator (t-PA) can dissolve local thrombi in blood vessels and recanalize a blocked vessel by activating plasminogen. At present, Genentech (USA) is the only entity that can produce recombinant human t-PA(rt-PA) at a large scale by means of genetic engineering technology and has developed successfully a rt-PA medicine. The first generation of rt-PA made in this company has become the treatment of choice for thrombotic diseases, but it has some shortcomings First, its price is rather high at $1375 per vial on the international market. Second, its function has some weak points: 1)short half-life, just 3 to 5 minutes; 2)low specific affinity with fibrin; 3) activity and efficacy should be further improved. A much higher dose should be given because of the short half-life. Low specificity and activity give rise to two results. On one hand, there is still 10-20% patient's thrombi that cannot be completely dissolved by rt-PA. On the other hand, it results in fibrinolysis over all the body and affects the normal blood clotting mechanism so as to cause severe complications such as bleeding, especially in the skull and digestive tract.

For the above reasons, some other companies have developed the second generation of rt-PA since the rt-PA was used in the clinical. They modified the rt-PA gene in order to eliminate or improve upon the above weak points. TNK-TPA is a kind of mutated form of rt-PA which is universally researched. For example, Keyt BA, Paoni NF, Refino rt CJ, et al proclaimed "a Faster-acting And More Potent Form of Tissue Plasminogen Activator" ((Proc Natl Acad Sci USA) 1997 Apr. 26; 91(9): 3670-4). It was constructed on the basis of three sites of the t-PA gene by site-directed mutation. Two sites are located in the Kringle function domain, T103N and Q117N; one site is located in the protease domain, "KHRR296-299AAAA" (K296A, H297A, R298A, R299A). T103N adds a glycosylation site which increases specificity of complexing of TNK-tPA and fibrin and decreases its cleanup rate; Q117N destroys combination of K1 region and mannose and the action domain of Kupffer cells in liver, and prolongs half-life; KHRR296-299AAAA destroys the functional region of PAI-1 and prolongs its half-life, too. As for the production of TNK-TPA, it is universal to adopt an ordinary eukaryotic gene expression vector, using CHO cells as the host cell. TNK-TPA integrates randomly into the expression system of the host cell genome. For example, Wu Benchuan, et al, announced the above expression system and preparation method of expressed protein in the article "Purification and identification of recombinant tissue-type plasminogen activator" published in <Development of Biochemistry and Biophysics> (1997, 24 (1):71-75).

DETAILED DESCRIPTION OF THE INVENTION

The inventor discovered two families carrying an extra bi-satellite microchromosome (BM) in these two families with 2 and 3 generations, the BM does no harm to human body. The families show a normal phenotype. Seventeen similar families are reported in the world, and nobody conceived of assembling human gene vector using the small chromosome elements. The applicant put forward the structure Using the FISH technique, it was found that the bi-satellite microchromosomes come from the short arms of human group D or G chromosomes 13, 14, 15, 21 and 22. The short arms of human group D or G chromosomes are nucleolus organizing regions abundant in ribosomal DNA (rDNA). Different polymorphisms with different length exist in these regions in human chromosomes, and the genes in these regions can be actively transcribed in the cell metaphase. Thus it was inferred that specific DNA fragments can be used as a targeting sequence if they were isolated from BM, and the gene of interest can be transferred into the nucleolus organizing region in the short arms of human group D or G chromosomes. There the gene should be relatively highly, stably and harmlessly expressed The following example can prove this strongly.

Figure 1:
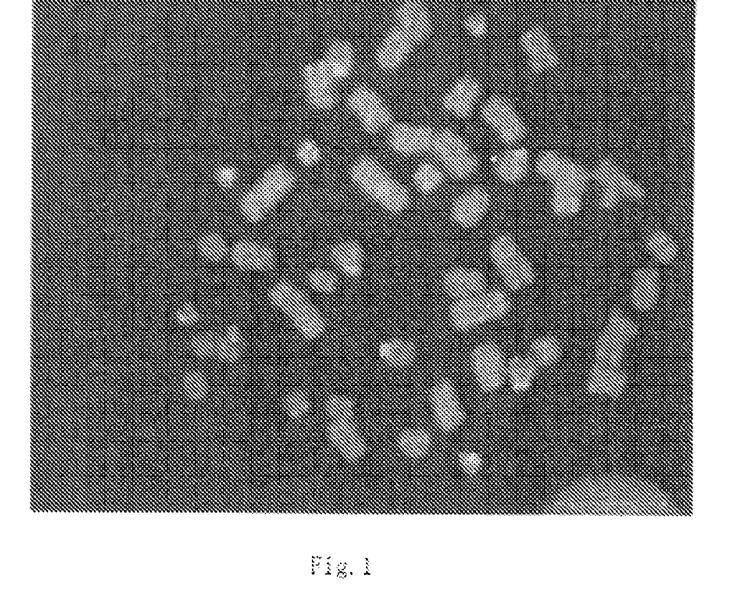
FIG. 1 shows FISH mapping of 120 kb BMSF fragment cloned in PAC.
Figure 2:
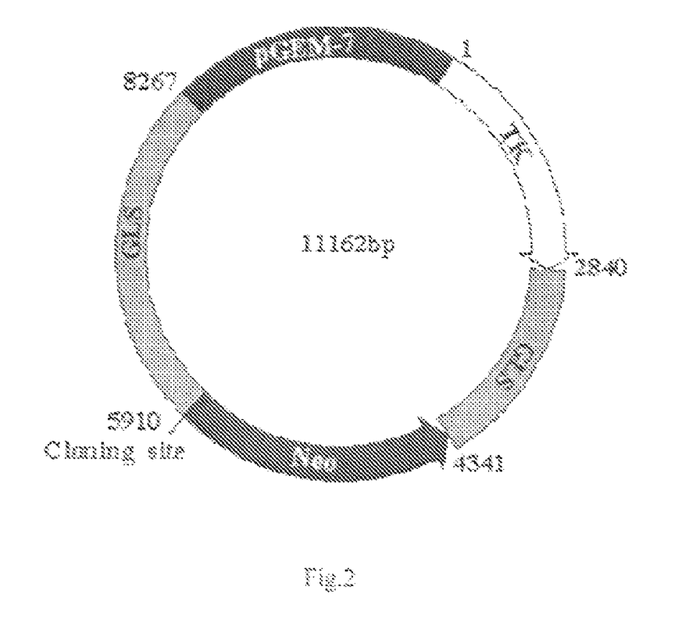
FIG. 2 is a circular map of the gene vector described in the invention (length of gene vector sequence: 1162 bp); pGEM-7 (8267-11162): vector replication component and prokaryote screening system; TK(1-2840): eukaryote negative screen gene, using TK promoter and TK polyA signal; Neo(4342—5910): eukaryote positive screen gene, using sv40 promoter and sv40 polyA signal; GLS (2841—4341, 5911—8267): leading sequence for gene targeting; Cloning site (5910): insert-site of desired gene

The inventor at first constructed a specific pUC19 library of the microchromosomes by a micro-dissection method and obtained a single copy fragment by screening the library The fragment was proved by the FISH technique to come from the short arms of human group D or group G chromosomes and the single copy was used as probe to screen a human PAC genomic library. Then, a 120 kb DNA fragment which comes from BM and short arms of human group D or group G chromosomes was confirmed by the FISH technique (FIG. 1). No gene concerned with important physiological function is found by analyzing sequence of this BM specific fragment (BMSF), so it is safe to take it as a target The applicant further used a small fragment from the BMSF as a targeting sequence to construct a gene vector.

Based on above evidence, a gene vector using a DNA sequence without vital physiological function-related gene or a DNA sequence with identity to short arms of human group D or G chromosomes as a targeting sequence can site-directly introduce a desired gene into the short arms of human group D or group G chromosomes and so the cell line according to the invention can then be obtained.

Different vectors can be constructed on the basis of the targeting sequence according to the present technique, and then one can obtain a recombinant vector-TNK-TPA by ligating a TNK-TPA gene into the constructed vector The methods used for constructing the targeting vector and the TNK-TPA vector are common in the art. Using the recombinant above, the desired gene TNK-TPA can be also transferred into a host cell by routine method.

The example of the invention gives in detail the identification of the 120 kb specific DNA sequence from short arms of human group D or group G chromosomes, and the construction of the vector using a 3.8 kb fragment from the 120 kb BMSF as a targeting ing sequence. The full sequence of the vector is given in SEQ ID NO: 1. Then a TNK-TPA gene as a desired gene is ligated into the vector and the recombinant vector-TNK-TPA is achieved. The inserting site of TNK-TPA gene is at nucleotide 5910 of the vector. The bacterial strain containing the recombinant vector-TNK-TPA is preserved in the China Typical Culture Collection Center (Wuhan University, China. Wuhan 430072) on Sep. 29, 2000. The collection number is CCTCCM200032. The depositor names it *Escherichia coli* JM109/JH-5/pNS-TPA.

According to the above methods, a novel cell line with the desired gene TNK-TPA integrated in the short arms of human group D or group G chromosomes of an *E. coli* HT1080 cell. The cell line was accepted by China Typical Culture Collection Center (Wuhan University, China. Wuhan 430072) on Aug. 18, 2000. The collection number is CCTCC C200006. The cell line is a human fibrosarcoma cell line, which is human gene-transformed cell. The depositor names it human fibrosarcoma cell line /JH-2/TPA. The preserved cell line is a pure cultivative cell line. The cells may be cultured in 10% calf serum in DMEM, pH 7.0-7.4, at 37° C.

The above cell line can substitute for transformed CHO transformed cells to prepare TNK-TPA.

The purified protein expressed by the cell line of the invention has been confirmed to be the desired protein by Western blotting and amino acid sequence analysis.

The invention provides a novel cell line by site-directedly transferring a recombinant human-source gene vector/TNK-TPA cDNA into D group and/or G group chromosomes of a human HT1080 cell and so provides a method to produce TNK-TPA Compared with the existing technology, the invention dramatically decreases cost of TNK-TPA because of its efficient and stable expression.

EXAMPLE 1

Preparation of a Gene Targeting Sequence of the Invention

1 Isolation of PAC Clone with Gene Targeting Sequence
1.1 Construct BM specific pUC19 library through microdissection, PCR, microcloning (Deng H-X, Yoshirua K, Dirks R W, et al. Hum Genet 1992,89:13.)
1.2 Identification of BM Specific Single Copy DNA (1) preparation of colony matrix membrane: draw 14×12 square wells on two nylon membranes, labeled as A and B, and put into two plates with solid LB, respectively, then pick white clones randomly from library plates and inoculate to the 14×12 square wells of two membranes with same coordinate, add 100 ng single copy DNA to the 13th line as positive control, and then add 100 ng gDNA to 14th line as negative control. Two plates are incubated for 10~12 hours at 37° C., and membrane B is stored at 4° C. Remove membrane A from plate, and treat on a filter paper soaked by following solution: 10% SDS, 5 minutes, 0.5N NaOH/1.5M NaCl, 3 minutes, 1.5M NaCl/0.5M Tris.HCl, 3 minutes, 2×SSC/0.2M Tris.HCl, 10 minutes, 80° C. vacuum dry 2 hours, keep for use.

(2)Preparation of gDNA Probe

Sample 50~75 ng gDNA, add sterile water to 11 ml, boil and denature at 100° C. for 10 minutes. The following system is used as a random primer labeling reaction:

| | |
|---|---|
| 2 mM dNTP(dATP⁻) | 3 µl |
| primer mixture | 2 µl |
| Klenow enzyme | 1 µl |
| α-$^{32}$p-dATP | 3 µl | vortex and mix up thoroughly, incubate 30 minutes at 37° C. Add 8 µl stop mixture, pass through G-50 column to purify probe, withdraw ⅒ of the mixture to conduct liquid scintillation.

(3) Hybridization: colony matrix membrane is immersed in 2×SSC 10 minutes, lightly wipe off colony fragments from the membrane surface. Pre-hybridize at 65° C. in 5 ml hybridization solution over 30 minutes. Sample probe solution to boil and denature 10 minutes at 100° C. according to the concentration of 1.2×10$^6$ cpm/ml and measure liquid scintillation value, add 5 ml fresh hybridization solution, hybridize with colony lattice membrane over 12 hours at 65° C., and wash membrane according to following conditions: 2×SSC/0.1% SDS, 10 minutes at room temperature, 2×SSC/0.1% SDS, 10 minutes at 65° C., 0.1% ×SSC/0.1% SDS, 10 minutes at 65° C., −70° C., autoradiograph. No or a weak hybridization signal is primarily regarded as single copy.

(4) Sequence analysis, Southern blotting: pick a clone from the corresponding position of membrane B, culture it in one small scale, sequence plasmid DNA extracted. The sequence of single copy DNA shows no similarity compared with the database of GenBank. At last, digest the plasmid by EcoRI enzyme and isolate the insert DNA by random primer method, label the insert by α-$^{32}$p-dATP and hybridize with gDNA digested by EcoRI on a piece of nylon membrane, those showing 1 or 2 hybridization bands are single copy DNA clones.

1.3 Identification of PAC Clone with BM Specific Sequence and Short Arms of Human Group D or Group G Chromosomes (1) Screen Human PAC gDNA and Acquire Positive Clone (2) Label 260 bp single copy probe P8-7 with α-$^{32}$p-dATP by random primer method→purify probe by G-50 column (medium granularity)→ready for use 4° C. →immerse 7 PAC membranes in 2×SSC 10 minutes→pre-hybridize 3 hours, 55° C. →denature probe 10 minutes, 100° C. →add to 50 ml hybridization solution purchased commercially to a final concentration of 4.6×10$^5$ cpm/ml and hybridize with PAC membrane 1 hour 65° C. →wash membrane: 2×SSC, once a time 10 minutes at room temperature, 2×SSC/0.1% SDS, 10 minutes at 65° C. twice→apply to X-ray film, autoradiograph at 70° C. 12 hours→develop X-ray film→read the positive clones.

(3) Randomly pick positive clones and number from five different plates, purchase PAC clone.

1.4 Hybridization of the DNA fragment in PAC clone with metaphase cells confirms that the insert DNA in positive PAC clone originates from short arms of human group D or group G chromosomes through FISH, as the FIG. 1 shows.

The above experimental methods refer to the Molecular Cloning written by J Sambrook et al., second Edition, Cold Spring Harbor laboratory Press, 1989.

2. Isolation of the targeting sequence. Main material: β-agarase(Bio-Labs), Not I Agarose (1) Digest the plasmid PAC169 by Not I enzyme (2) Isolate an around 120 kb insert DNA through PFGE.

Pulse electrophoresis conditions electrophoresis buffer: 0.5× TBE High strength Analytical Grade Agarose: (Bio-Rad, low Melting point agarose LMP) 1%, Switch time: from two to fifteen second, electrophoresis time: 18 h. voltage: 6v/cm, angle: 120°, temperature: 14° C.

(3) After electrophoresis, stain the gel with EB (0.2 ug/ml) thirty minutes. According to the Marker display, cut that 120 kb DNA band with sterile knife.

(4) Treat the gel cut out by β-agarase and precipitate with enthanol.

EXAMPLE 2

Preparation of Gene Vector of the Invention

1. The Construction of Gene Vector and Induction of Target Gene 1.1 Construct Gene Vector 1.1.1 Nsi I and Stu I (blunt enzyme) digest PAC DNA, run the sample on a common agarose gel, recover the 3.8 kb DNA and purify the DNA by electric elution.

1.1.2 pGEM-TK vector DNA is digested with Hind III, and then digested with Klenow further to generate the blunt ends.

1.1.3 The blunt ends of pGEM-TK/Hind III is further digested with Nsi I.

1.1.4 The purified 3.8 kb/Nsi I+Stu I digested DNA and the Nsi I digested pGEM-TK are ligated for 17 hours at 16° C.

1.1.5 The ligated product is transformed into JM109 competent bacteria, culture 19 hours at 37° C. in an ampicillin plate.

1.1.6 Randomly pick single clones and identify the positive clones with Nsi I and Nhe I double digestion.

1.1.7 The plasmid pCDN-GPR is digested with Xba I and Nhe I to acquire the XbaI+NheI digested Neo gene.

1.1.8 Construct pNS2 gene vector by ligating the XbaI+NheI digested Neo gene with the pGEM-TK-3.8 kb/Nhe I fragment.

2.1 Induction of TNK-TPA Gene 2.1.1 Clone TNK-TPA (CDS) into pcDNA 3.1(-).

2.1.2 Design the primers TPCF and TPCR to amplify TNK-TPA gene and expression element (CMV promoter and BGH polyA signal), Avr II restrictive sites are added to the two ends of the primers.

```
Primer Sequence:                       (SEQ ID NO:2)
TPCF:            ATGCATCCTAGGGGAGGTCGCTGAGTAGTG
                       AvrII (SEQ ID NO:3)
TPCR:            TGCATGCCTAGGTACCCCCTAGAGCCCAG
                       AvrII
```

2.1.3 Digest TNK-TPA gene and expression element (CMV promoter and BGH polyA signal) with AvrII, ligate it to the pNS2 vector digested with Nhe I.

2.1.4 Transform the ligated product into recombinant JM109 *E. coli* to obtain a bacterial strain containing the vector-TNK-TPA (collection number is CCTCC M200032).

The above experimental methods refer to the Molecular Cloning written by J Sambrook et al., second edition, Cold Spring Harbor laboratory Press. 1989.

3 The Gene Vector Extraction 3.1 Material 3.1.1 QIAGEN Plasmid Maxi Kit 3.1.2 Culture Medium: Liquid LB

| | |
|---|---|
| Trypton | 5 g |
| Yeast extract | 2.5 g |
| NaCl | 2.5 g |
| Add H$_2$O to | 500 ml |
| Sterilize by autoclaving | |

3.1.3 Ampicillin: 100 mg/ml (1000×)

3.2 Method

1) Pick positive single clones and inoculate them in 3 ml LB (Amp+), incubate for 1 h at 37° C., 250 rpm.
2) Inoculate 100 ul of primary culture in 100 ml LB (Amp+), incubate for 16 h at 37° C., 250 rpm.
3) Harvest the bacteria by centrifugation at 6000×g for 15 minutes at 4° C.
4) Resuspend the bacterial pellet in 10 ml of buffer P1.
5) Add 10 ml of buffer P2, mix gently but thoroughly 6 times, and incubate at room temperature for 5 minutes.
6) Add 10 ml of chilled buffer P3, mix gently by inverting 6 times, and incubate on ice for 20 minutes.
7) Centrifuge at 2000×g for 30 min at 4° C.
8) Transfer supernatant containing plasmid DNA promptly into a 40 ml high-speed centrifuge tube and centrifuge at 2000×g for 15 min at 4° C.
9) Equilibrate a QIAGEN tip 500 by applying 10 ml buffer QBT.
10) Transfer the supernatant to the QIAGEN-tip 500 and allow it to pass through this column.
11) Wash the QIAGEN-tip with 30 ml buffer QC.
12) Elute DNA with 15 ml QF and collect elution.
13) Precipitate DNA by adding 10.7 ml (0.7 volumes) isopropylalcohol to the elution, mix up.
14) Centrifuge immediately at 15000×g for 30 min at 4° C.
15) Remove the supernatant, wash DNA pellet with 5 ml of 70% ethanol and centrifuge at 15000×g for 10 min.
16) Remove the 70% ethanol, air-dry the pellet for 10 min, and dissolve the DNA in TE solution.

EXAMPLE 3

Transfer the recombinant vector-TNK-TPK acquired in the example 2 into host cell HT1080, obtain the required cell lines after screening, and express in vitro, confirms site-directed integration and high efficiency expression.

1 Material 1.1 Cell: HT1080

Culture Medium: High Sugar DMEM+10% FBS (HT1080) EMEM+10% FBS 1.2 Electroporation apparatus: purchased from Bio-Rad Company.

2. Methods

1) Culture the cells in a 75 cm$^2$ culture bottle to 70%~80% confluence.
2) Harvest the cells and wash with HeBs Buffer for two times, then account the cells.

3) Centrifuge at 15000 rpm at 4° C. for 10 min.
4) Resuspend the cells with a reasonable volume of HeBS Buffer to make the cell density to $10^6$~$10^7$/ml.
5) Add 0.8 ml suspension (about 10 μg DNA vector) to an 0.4 cm electroporation cuvette
6) Electroporate the suspension, parameters: 260V, 550 uF for 11~13 ms.
7) Transfer the shocked cells to a 75 cm$^2$ culture flask, add 14 ml culture medium with ampicillin/streptomycin, then culture in 37° C., 5% $CO_2$ for 24~48 hrs.
8) Screen the cell with G418 (final concentration of 300 μg/ml), change medium every 2-3 days, in parallel, normal cells are used as a control.
9) Calculate the survival clone number in transfected cells after normal cells completely die in 7-10 days, and then add G418 (150 μg/ml) to maintain surviving clones.
10) Continue to screen the transfected cells with GCV (the ultimate concentration of 500 ng/ml)
11) Most cells die in 7-10 days, add GCV 250 μg/ml to remaining living cells or withdraw GCV, culture the cell up to 70%~80% confluence, and determine the expression activity of the transfected gene.

3 Results

Figure 3:
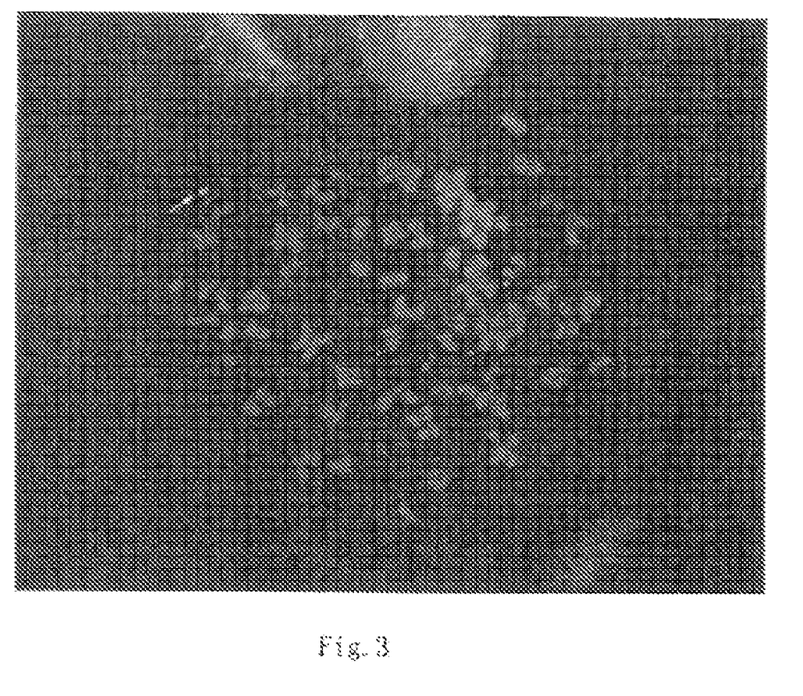
FIG. 3 is FISH mapping of targeted TNK-TPA gene in positively a transformed cell colony. This revealed that the TNK-TPA gene has been site-directedly transferred into the short arms of human group D or group G chromosomes by the vector.

The TNK-TPA gene with the vector were transferred into HT1080 cells by electroporation and the positive cell lines were obtained after positive and negative screening (Collection NO. CCTCC: C200006), and confirmed to be site-directed insertion by FISH (FIG. 3). The results of assay of TNK-TPA activity are shown in Table 1.

Figure 4:
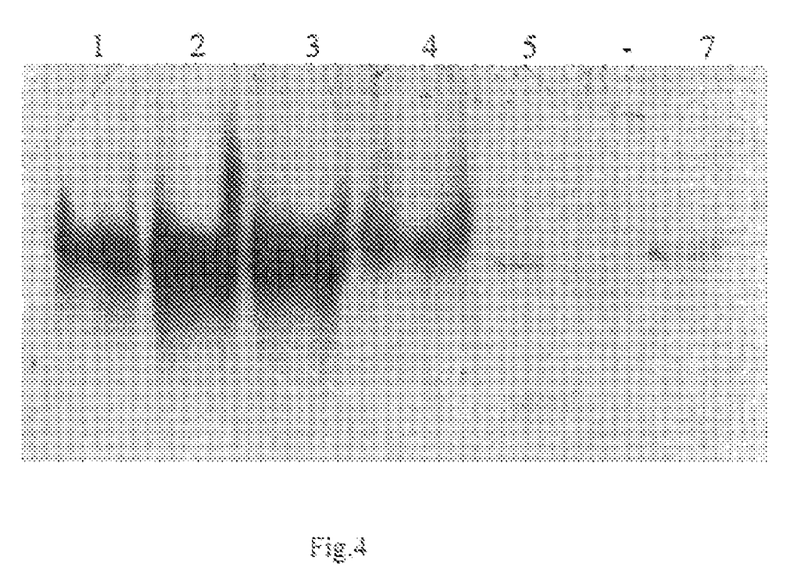
FIG. 4 is Western blotting result of purified TNK-TPA protein, 1~4 are purified TNK-TPA protein, "–" denotes negative control.

Expression activities are: negative control HT1080 cells is 0 U/106 cells/24 hrs, the positive HT1080 cells is 408 U/106/24 hrs after transfer and 407 U/106 cells/24 hrs after 95 days. The expression of TNK-TPA is highly stable. In addition, the expressed protein of TNK-TPA is proved by Western Blotting and amino acid sequencing (FIG. 4).

TABLE 1

The results of activity assay of TNK-TPA for positive HT1080 cells(ug/$10^6$ cells/24 hrs)

| The days of transfer | T1* | The days of transfer | T15* |
|---|---|---|---|
| 33 | 408 | 54 | 188 |
| 37 | 396 | 58 | 204 |
| 60 | 411 | 95 | 114 |
| 68 | 430 | | |
| 74 | 430 | | |
| 88 | 441 | | |
| 90 | 440.9 | | |
| 95 | 407 | | |

*T1, T15 are two positive cell lines expressing TNK-TPA

4 The Technology of TNK-TPA Protein Preparation
1) Culture TNK-TPA/HT1080 cell line with DMEM medium till 80% confluence, and continue to culture them with serum-free, collect the supernatant after 24 hrs which containing expressed TNK-TPA;
2) Filtrate the supernatant with 0.22 μm filter membrane.
3) Concentrate the filtrate 7 times with 10 KD ultrafiltration membrane.
4) Pass through PROSEP-LYSINEII chromatography media column.
5) Wash out the nonspecific protein absorbed on the column with 5× column volume of 0.05M PB buffer (pH 7.0).
6) Elute TNK-TPA protein bound to the column with 0.2M Arginine/0.05M PB (PH7.5);
7) Desalt protein solution with 3 KD ultrafiltration membrane, lyophilize it into powder dosage.

The invention claimed is:

1. A human fibrosarcoma cell line deposited as CCTCC C200006.

2. An *Escherichia coli* strain deposited as CCTCCM200032.

* * * * *